United States Patent [19]

Brignola

[11] 4,331,146
[45] May 25, 1982

[54] SYRINGE ASSEMBLY

[75] Inventor: Dominic J. Brignola, Phoenixville, Pa.

[73] Assignee: The West Company, Phoenixville, Pa.

[21] Appl. No.: 34,461

[22] Filed: Apr. 27, 1979

Related U.S. Application Data

[63] Continuation-in-part of Ser. No. 753,954, Dec. 23, 1976, abandoned, which is a continuation of Ser. No. 467,790, May 7, 1974, abandoned, which is a continuation-in-part of Ser. No. 399,729, Sep. 21, 1973, abandoned, which is a continuation-in-part of Ser. No. 182,759, Sep. 22, 1971, abandoned.

[51] Int. Cl.³ .............................................. A61M 5/00
[52] U.S. Cl. ............................................. 128/218 DA
[58] Field of Search ........ 128/218 N, 218 D, 218 DA, 128/218 M, 272.1, 221, 215, 234

[56] References Cited

U.S. PATENT DOCUMENTS

| | | | |
|---|---|---|---|
| 3,685,514 | 8/1972 | Cheney | 128/218 M |
| 3,838,689 | 10/1974 | Cohen | 128/218 M |
| 3,976,069 | 8/1976 | Ong | 128/218 DA |

FOREIGN PATENT DOCUMENTS

| | | | |
|---|---|---|---|
| 867922 | 4/1971 | Canada | 128/218 DA |
| 1491785 | 10/1969 | Fed. Rep. of Germany | 128/218 M |

Primary Examiner—John D. Yasko
Attorney, Agent, or Firm—Eugene E. Renz, Jr.

[57] ABSTRACT

A syringe assembly comprising a casing for a medicament or the like having a discharge opening at one end, a diaphragm assembly mounted at said end normally sealing said contents, plunger means movable in said casing and operable upon displacement in one direction to effect increase in pressure in said casing to rupture or displace said diaphragm to permit discharge of the contents of said casing.

12 Claims, 53 Drawing Figures

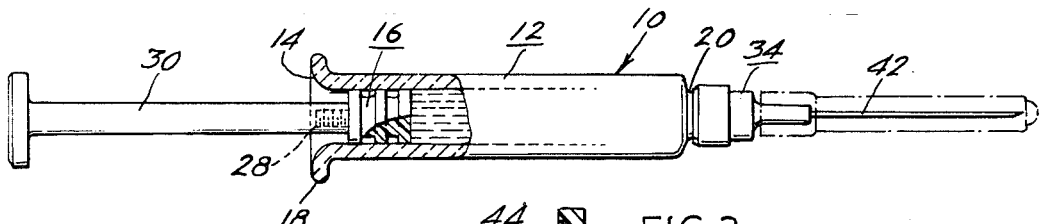
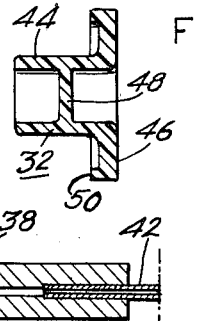
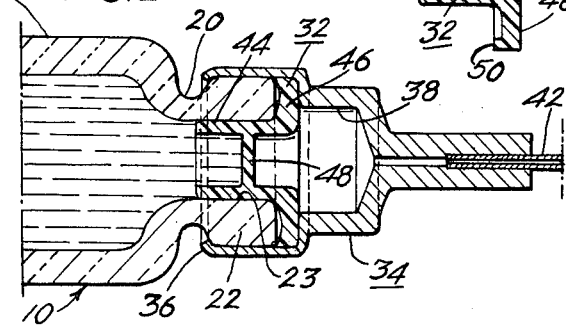
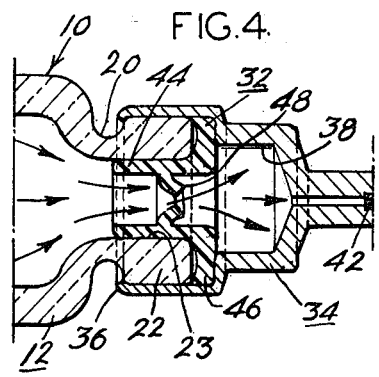
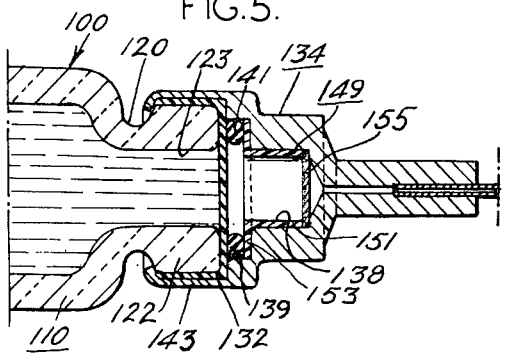
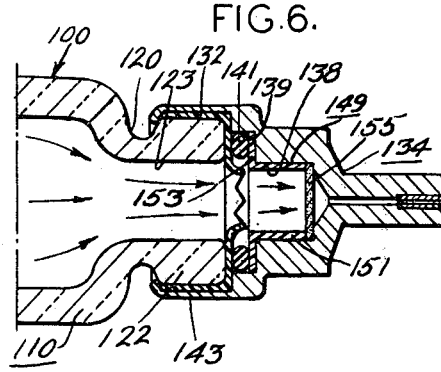
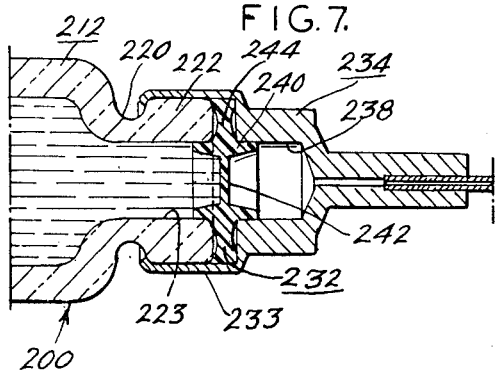
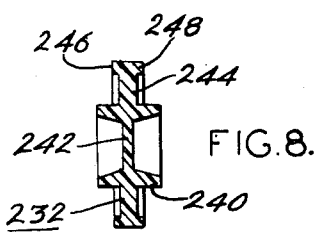

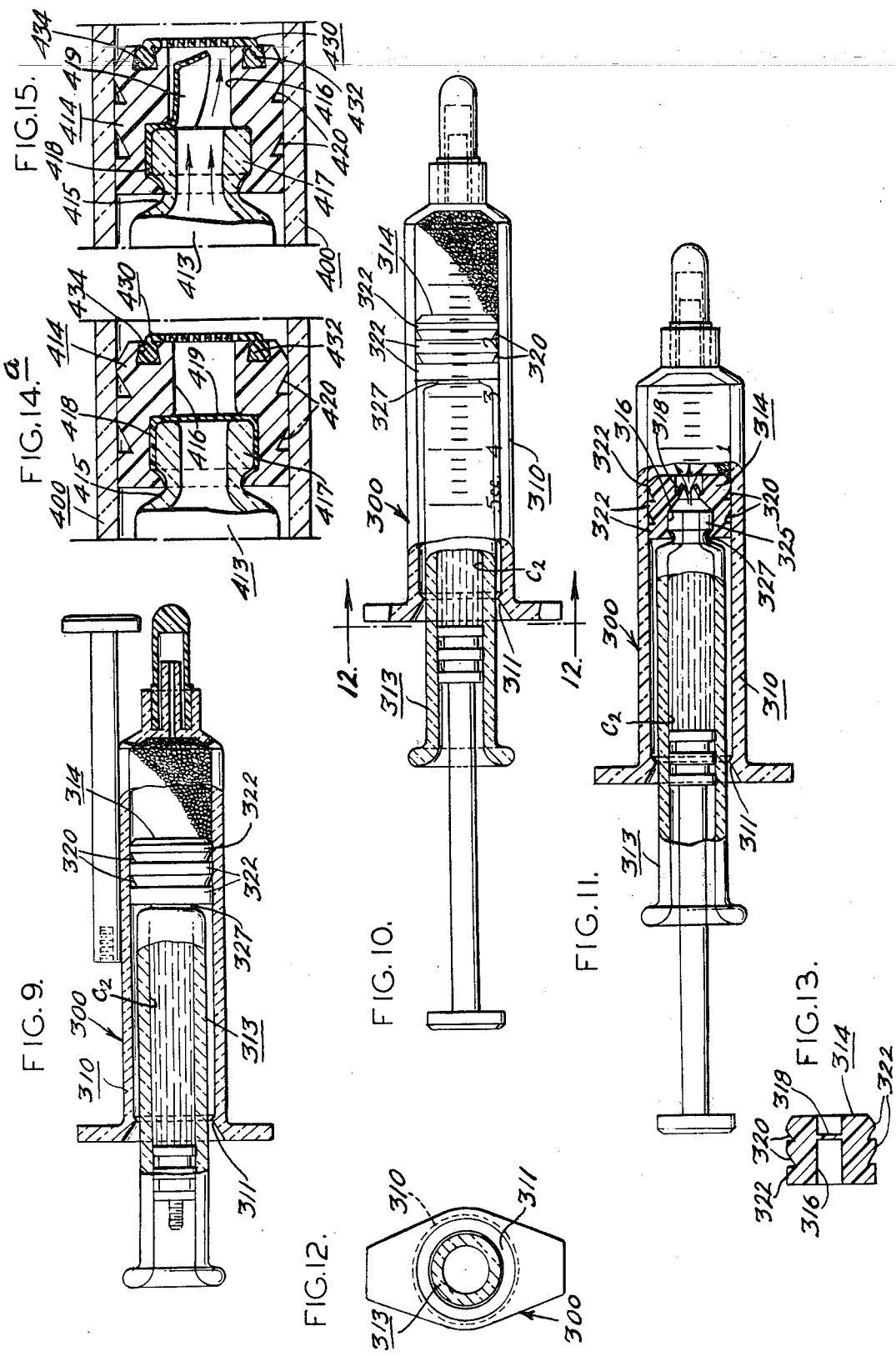

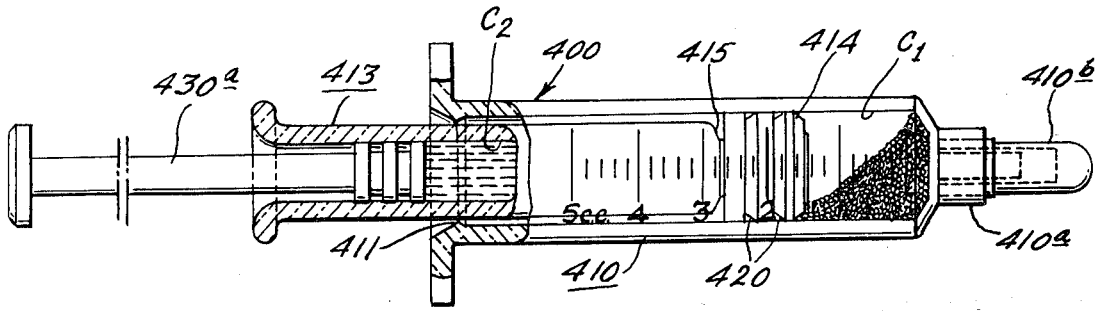
FIG.14.
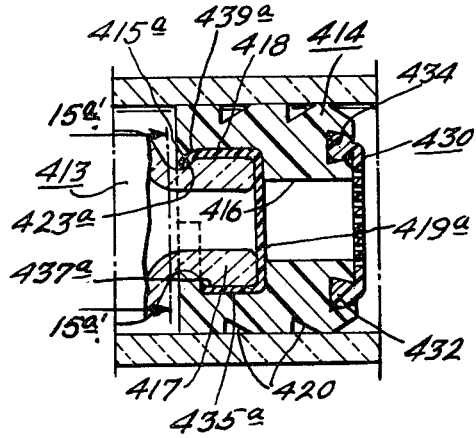
FIG.15ª.
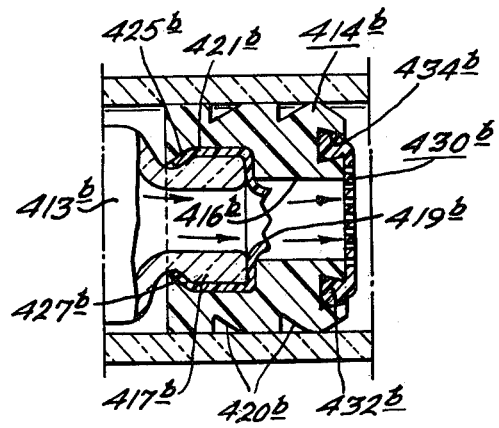
FIG.15ᵇ.
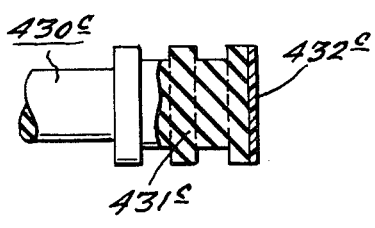
FIG.15ᵉ.
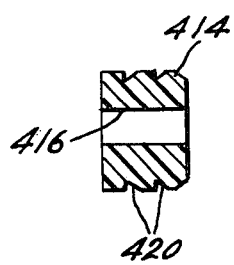
FIG.15ᵈ.
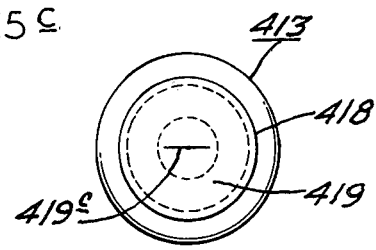
FIG.15ᶜ.
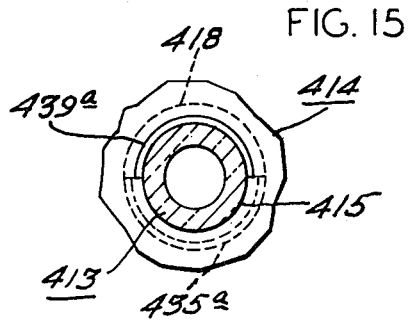
FIG.15ªʹ.

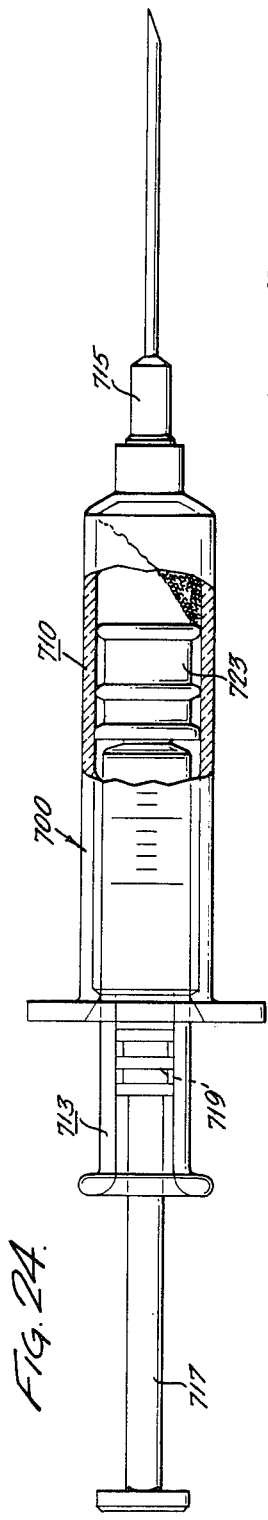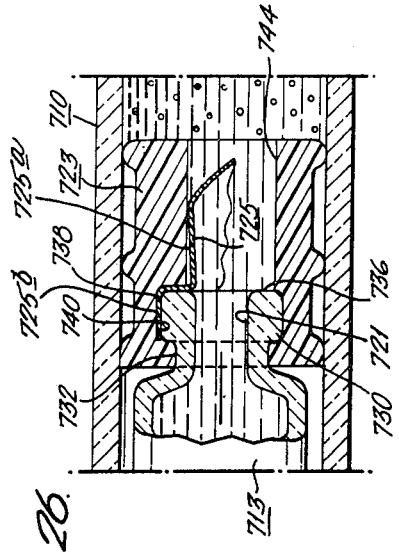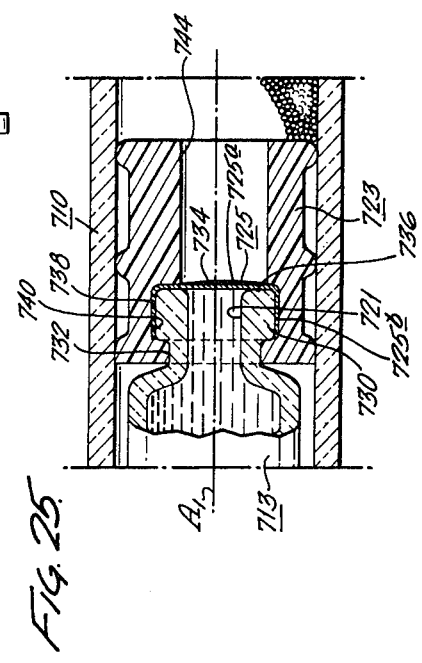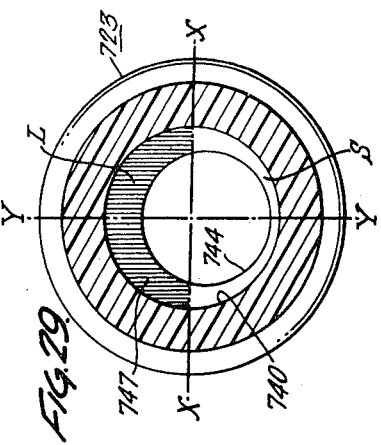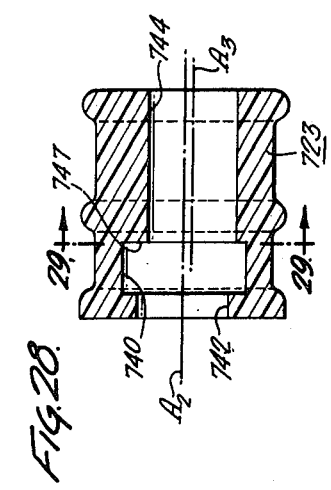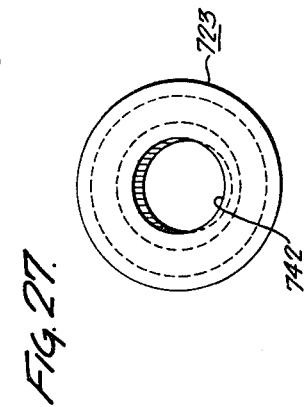

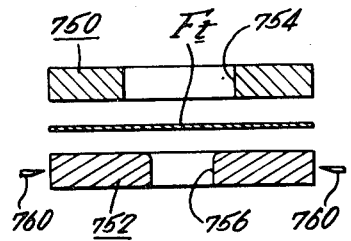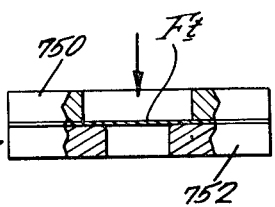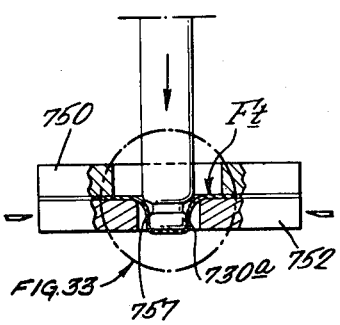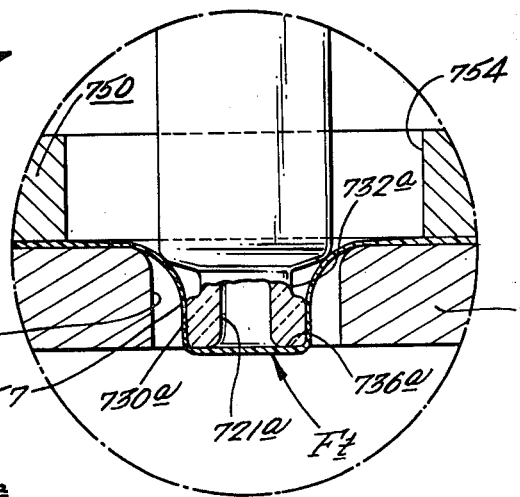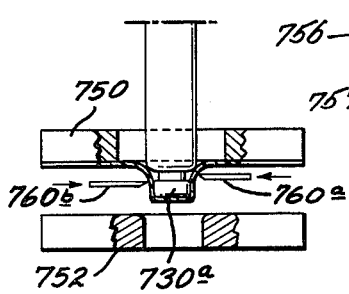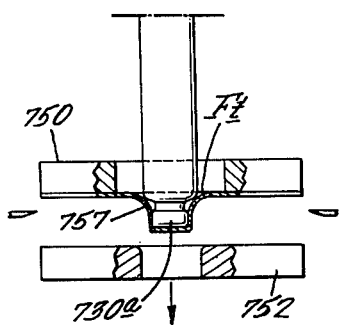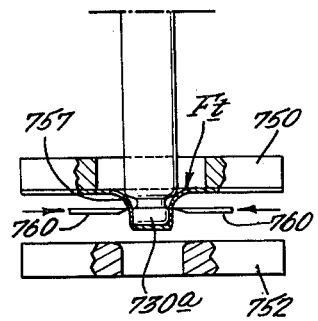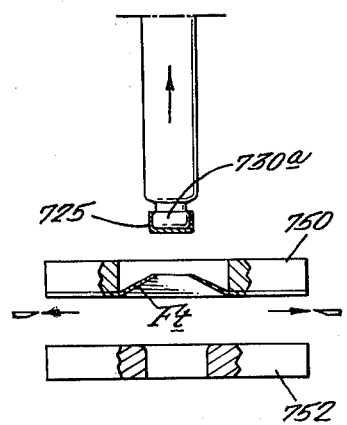

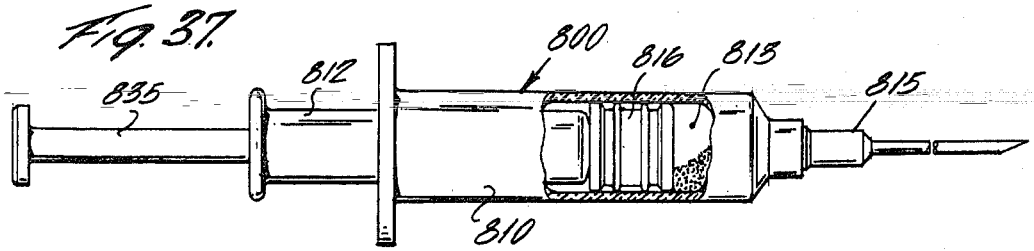
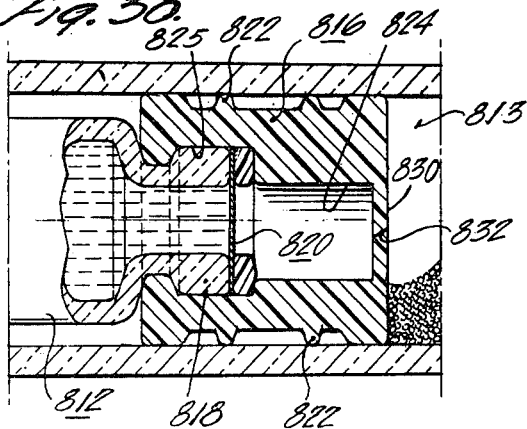
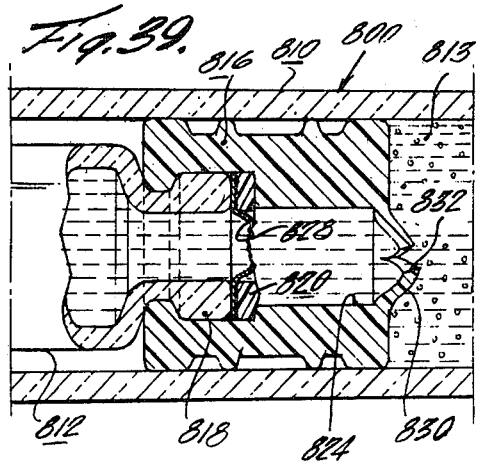
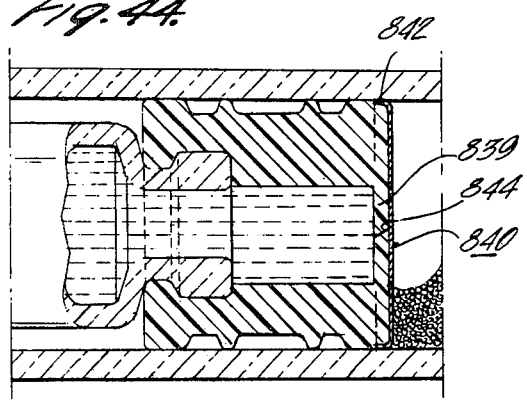
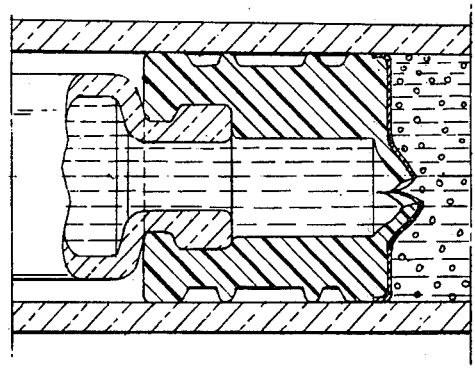
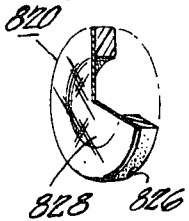
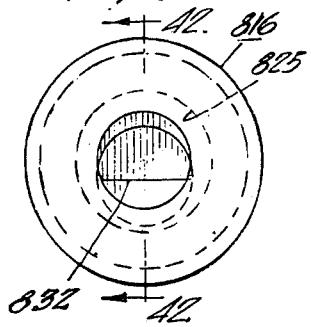
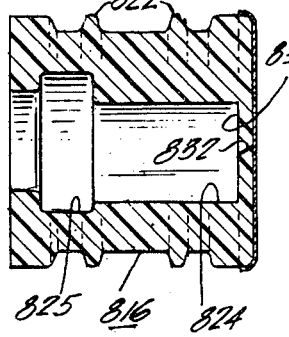
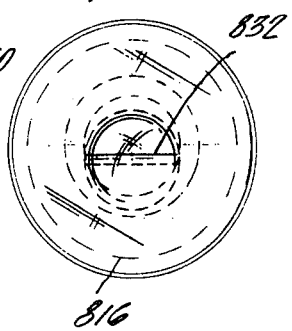

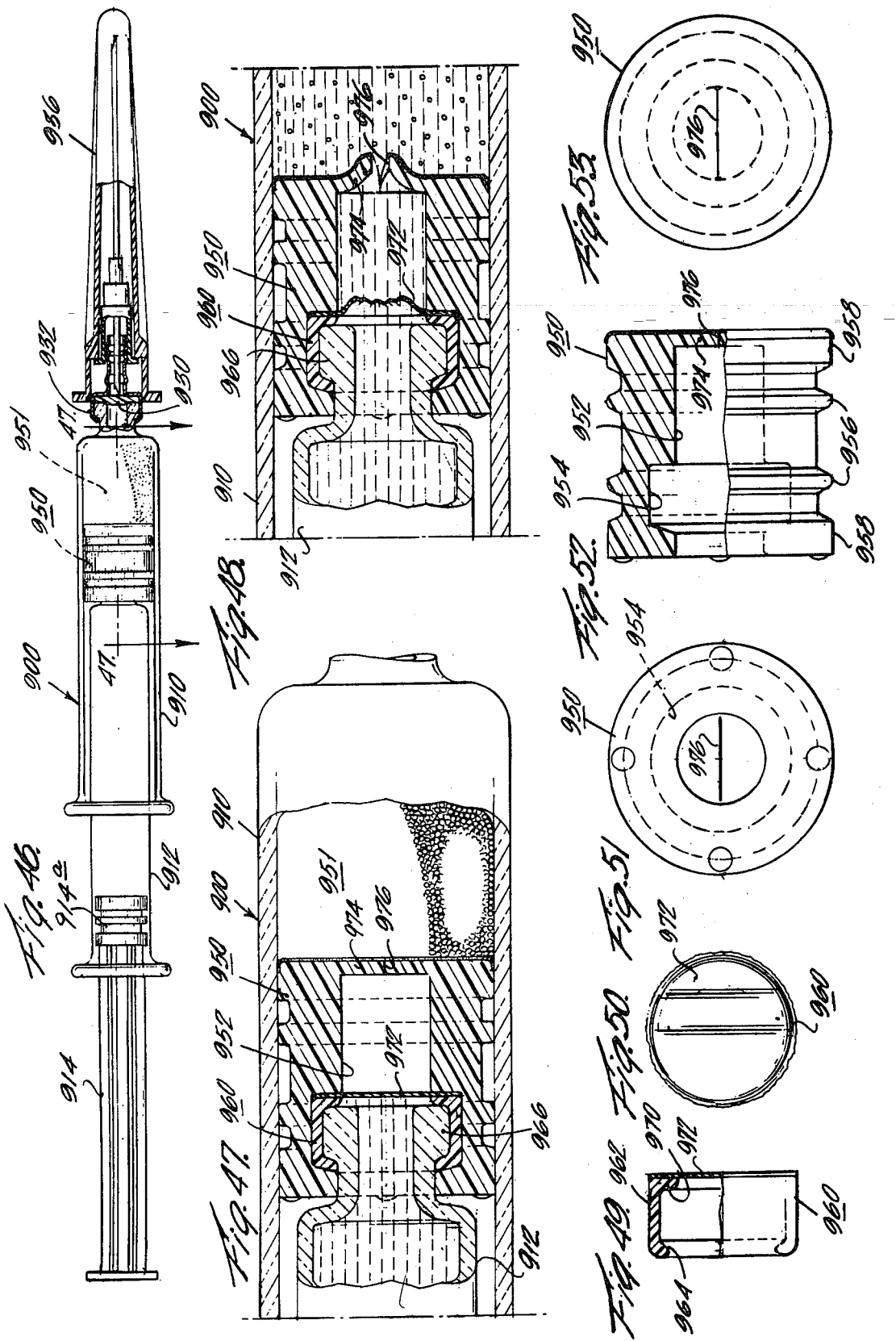

SYRINGE ASSEMBLY

This application is a continuation-in-part of my prior application Ser. No. 753,954 filed Dec. 23, 1976, now abandoned, for SYRINGE ASSEMBLY which in turn is a continuation of my prior application Ser. No. 467,790 filed May 7, 1974, now abandoned, for SYRINGE ASSEMBLY which in turn is a continuation-in-part of my prior application, Ser. No. 399,729, filed Sept. 21, 1973, entitled SYRINGE ASSEMBLY, now abandoned, which in turn is a continuation-in-part of my prior application, Ser. No. 182,759, filed Sept. 22, 1971, entitled SYRINGE ASSEMBLY and now also abandoned.

The present invention relates to cartridges for medicaments and more specifically to a syringe assembly for administering fluid medications to a patient.

These assemblies generally conprise a vial or container for the medicament, a plunger assembly for aspirating or discharging the contents through a needle mounted at the opposite end of the vial. Generally, these assemblies further include a sealing means in the form of a diaphragm disposed at the discharge end of the vial and which is adapted to be punctured by, for example, the pointed inner end of the needle when it is desired to discharge the contents of the vial. It has been found that in these assemblies there is the problem of "coring"; that is, entrapment of a plug of the rubber diaphragm in the syringe which makes it difficult to discharge the contents and presents the danger of injecting the core into the patient. Additionally, it has been found that these assemblies are comparatively complicated and difficult to assemble to insure a tight seal prior to use.

The present invention provides a syringe assembly which eliminates the problem of coring and provides an extremely effective means for sealing the contents prior to use. Further, the syringe assembly of the present invention is easy and economical to manufacture, assemble and use. Additionally, in one form of the invention the diaphragm is in the form of a bag which closes the discharge end of the vial and which, when hydraulic pressure builds up during initial movement of the plunger to discharge the contents, displaces to permit flow of contents through the discharge of the vial or container. An advantage of this so called "clip-off" diaphragm arrangement is that there is no particulation which could contaminate the medicament.

Another feature of the present invention is the provision of a method for assembling a diaphragm made of a stretchable material over the discharge end of a container to provide a mechanical bond therebetween Teflon and a medicament container for example, a syringe made of glass.

These and other features of the present invention and the various details thereof are hereinafter more fully set forth with reference to the accompanying drawings, in which;

FIG. 1 is a side elevational view partly in section of a syringe assembly constructed in accordance with the present invention;

FIG. 2 is an enlarged sectional view of the discharge end of the syringe;

FIG. 3 is a sectional view of the diaphragm;

FIG. 4 is a sectional view similar to FIG. 2 showing ruptured diaphragm during aspiration of the contents;

FIG. 5 is an enlarged sectional view of the discharge end of another embodiment of syringe in accordance with the present invention;

FIG. 6 is a view similar to FIG. 5 showing the ruptured diaphragm;

FIG. 7 is an enlarged sectional view of still another embodiment of diaphragm for a syringe in accordance with the present invention;

FIG. 8 is a sectional view of the diaphragm prior to assembly;

FIG. 9 is a side elevational view with parts in section of a two compartment syringe assembly constructed in accordance with the present invention;

FIG. 10 is a side elevational view with the actuating plunger in a retracted position;

FIG. 11 is a view similar to FIG. 10 showing the actuating plunger in an extended position to effect mixing of the fluid and dry product;

FIG. 12 is a sectional view taken on line 12—12 of FIG. 10;

FIG. 13 is a sectional view of the actuating plunger diaphragm;

Figure 16:
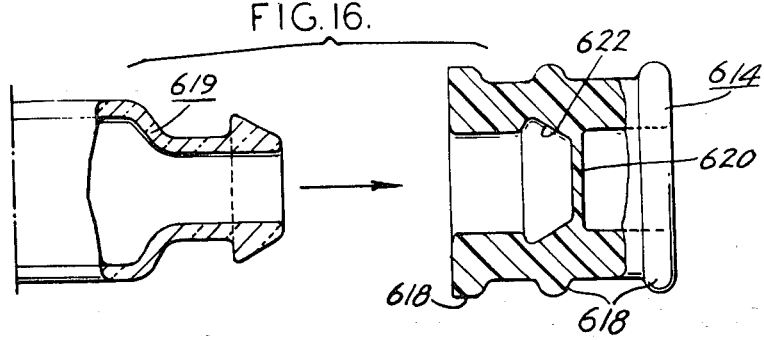

FIGS. 14, 14a, 15, 15a, 15a', 15b and 15c are views of a two compartment syringe assembly in accordance with the present invention illustrating various diaphragm arrangements;

FIG. 15d is a sectional view of a plunger for the inner container;

FIG. 15e is an enlarged sectional view of a piston plunger for use in a single or two compartment syringe in accordance with the present invention;

FIG. 16 is an exploded view partly in section of a modified form of barrel plunger assembly in accordance with the present invention;

FIGS. 17-23 inclusive show various embodiments of plunger assemblies in accordance with the present invention;

FIG. 24 is a side elevational view with parts broken away of another embodiment of syringe assembly constructed in accordance with the present invention;

FIG. 25 is an enlarged sectional view of the discharge end of the secondary barrel of the syringe prior to actuation of the diaphragm closing the discharge end;

FIG. 26 is a view similar to FIG. 25 showing the diaphragm in an actuated position for mixing of the diluent and dry product;

FIG. 27 is an end view of the secondary barrel plunger;

FIG. 28 is a transverse sectional view of the secondary barrel plunger;

FIG. 29 is a sectional view taken on lines 29—29 of FIG. 25;

FIGS. 30-36 inclusive are views showing the steps of a method in accordance with the present invention for applying a diaphragm to the discharge end of a barrel for a syringe assembly;

FIG. 37 is a side elevational view with parts broken away of a still further embodiment of syringe assembly in accordance with the present invention;

FIG. 38 is an enlarged fragmentary transverse sectional view showing the plunger mounted on the inner barrel showing parts of the assembly including the plunger and discharge end of the inner barrel in a storage position;

FIG. 39 is a fragmentary sectional view similar to FIG. 38 showing the same parts in an activated position;

FIG. 40 is a perspective view of the diaphragm of the syringe assembly of FIG. 38;

FIG. 41 is a rear plan view of the inner barrel plunger;

FIG. 42 is a transverse sectional view taken on lines 42—42 of FIG. 41;

FIG. 43 is a front plan view of the inner barrel plunger;

FIG. 44 is a transverse sectional view of a modified inner barrel plunger arrangement in a storage position;

FIG. 45 is similar to FIG. 44 with the plunger in an activated position;

FIG. 46 is a side elevational view of still a further embodiment of syringe assembly in accordance with the present invention with some parts broken away to show the internal construction more clearly;

FIG. 47 is an enlarged fragmentary sectional view taken on the line 47—47 of FIG. 46 showing parts of the assembly in a storage position;

FIG. 48 is a sectional view similar to FIG. 47 with the parts in an activated position;

FIG. 49 is a side elevational view of the diaphragm of the syringe assembly;

FIG. 50 is a front plan view thereof;

FIG. 51 is a rear plan view of the inner barrel plunger;

FIG. 52 is a side elevational view thereof partly in section; and

FIG. 53 is a front plan view of the plunger.

DESCRIPTION OF THE PREFERRED EMBODIMENTS

Referring now to the drawings and particularly to the first embodiment illustrated in FIGS. 1-2, inclusive, the syringe assembly generally designated by the numeral 10 includes a barrel or container 12 made, for example, of glass or other glass-like materials which is open at one end as at 14 to receive an actuating plunger 16. The container 12 as illustrated has an outwardly flared flange 18 at its open outer end and terminates at the discharge end in a reduced neck portion as at 20, the neck portion having an enlarged circumferentially extending bead 22.

The plunger or piston assembly 16 as illustrated has a threaded stud 28 which detachably mounts a plunger rog 30 which, as explained in more detail hereinafter, is used to discharge the liquid medicament from the vial.

A diaphragm 32 is mounted over the discharge opening 23 in the opposite end of the vial compartment and, in the present instance, is secured in place by means of a needle hub 34 having a circumferential flange which overlies the bead 22 and is held thereto by crimping or spinning the inner terminal edge over as at 36. The hub has a cavity 38 formed therein on the opposite side of the diaphragm 32 and an axial bore within which is mounted the hypodermic needle 42.

Considering now the specific arrangement of the diaphragm, the diaphragm 32 has a generally cylindrical body portion 44 which is of a size to snugly engage the discharge opening 23, the outer end of the body portion 44 having a radially outwardly directed circumferentially extending flange 46 which in the assembled relation seats against the axial end face of the bead 22. Approximately centrally of the body portion there is a thin membrane 48 which is adapted to be burst by hydraulic pressure as illustrated in FIG. 4 so that the liquid medicament may be discharged to the chamber 38 through the needle into the patient. As illustrated, the flange 46 terminates in a rearwardly directed circumferentially extending rib 50.

The syringe assembly of the present invention is very simple and economical to manufacture and assemble. For example, the diaphragm 32 is simply pressed into the discharge end 23 of the syringe compartment. Thereafter the hub assembly 34 is positioned over the diaphragm and crimped as at 36 to complete the assembly. In use of the syringe, the vial compartment is filled with a liquid medicament and then the plunger 16 is assembled to seal the contents. Initially, the plunger rod may be stored separately and when it is desired to use the syringe to inject the medicament, the plunger rod is simply threaded onto the piston 16 and, by moving it axially inwardly, the hydraulic pressure exerted on the membrane 48 effects bursting thereof without the use or need of independent piercing means. The medicament may then be discharged.

There is illustrated in FIGS. 5 and 6 another form of bursting diaphragm for a hypodermic syringe in accordance with the present invention. The syringe assembly which is generally designated by the numeral 100 includes a vial or container 110 made, for example, of glass which is similar to the vial or container of the embodiment discussed above and has a reduced neck portion as at 120 and a discharge end which terminates in an enlarged circumferentially extending bead 122 defining a discharge opening 123. The needle hub 134 supports a diaphragm 132 over the discharge end. The needle hub has an enlarged cavity 138 and a stepped shoulder configuration as at 139 to support an O-ring type seal 141 firmly presses the diaphragm against the axial end face of the head 122 at the discharge end. The hub has a collar 143 which is crimped or spun over the inner edge of the bead at 122 to hold the hub in place and firmly mount the diaphragm in sealing relation over the discharge end of the vial. The diaphragm 132 as illustrated is cupped-shaped and preferably made of an impermeable, inert, fragible material, for example, a polymeric tetrafluoroethylene such as Teflon, and is of a predetermined cross-section so that upon fluid pressure buildup in the vial it can be burst in the manner shown in FIG. 6.

In the use of the syringe described, the barrel is filled with a liquid medicament and thereafter the plunger assembly, not shown, is inserted into the upper end of the barrel. When it is desired to use the syringe to discharge the medicament, the plunger rod is simply actuated axially inwardly and the hydraulic fluid pressure buildup bursts the diaphragm so that the medicament passes through a filter assembly 149 into the compartment 138 of the needle hub and then through the needle into the patient. It is noted that the bursting of the Teflon diapharagm produces a "popping" sound evidencing that the contents have been maintained in a sealed environment. As illustrated, the filter assembly 149 comprises a cylindrical member 151 having an outwardllly directed flange 153 at its inner end which mounts a fine mesh filter 155 across the outer end of the cup. The cylindrical member and flange may be made of a plastic material.

There is shown in FIG. 7 another embodiment of syringe assembly in accordance with the present invention. The assembly which is broadly designated by the numeral 200 includes a vial or container 212 made, for example, of glass which is open at its outer end to receive a plunger assembly generally of the type illustrated in the first described embodiment and has a reduced neck portion 220 at its outer terminal end defining a discharge opening 223. The neck portion terminates in an enlarged circumferentially extending bead 222. The needle hub 234 is generally similar to the configuration of the needle hub for the first described embodiment and includes a reservoir 238 and a flange 233 which is crimped or spun at its inner terminal end over the bead 222 to hold the diaphragm 232 in place over the discharge opening of the vial.

The diaphragm 232 which is best illustrated in FIG. 8 has a generally cylindrical body portion 240 of a diametral dimension to snugly engage in the discharge opening and into the entrance end of the reservoir 238 in the manner illustrated in FIG. 7. The body portion 240 is divided in halves by a rupturable wall 242 and, as illustrated, the inner face of the body portion on either side of the wall 240 is frusto-conical and tapers inwardly toward the wall 242 at a slight angle. The diaphragm further includes a radially outwardly directed web portion 244 which at its outer peripheral edge has oppositely directed axially extending ribs 246 and 248. This assembly provides an extremely effective fluid-type seal when it is mounted in place in the manner shown in FIG. 7. Additionally, the symmetrical configuration of the diaphragm makes it extremely simple to assemble since it can be inserted into the discharge end of the vial from either axial end.

The assembly and use of this syringe is identical to the previously described embodiments. In other words, the compartment is filled with a liquid medicament and the plunger assembly inserted in place. Of corse, the diaphragm and needle hub are assembled to the discharge end prior to filling of the compartment. Now, when it is desired to discharge the contents, the plunger is moved axially inwardly and the fluid pressure buildup results in bursting of the center wall 242 of the diaphragm to permit flow of the liquid medicament to the reservoir 238 and then through the needle into the patient.

There is shown in FIGS. 9-13 inclusive, still another embodiment of syringe employing a rupturable diaphragm in accordance with the present invention. This syringe which is a two-compartment syringe is generally designated by the numeral 300 and includes an outer barrel or container 310 which is open at its upper end as at 311 and an inner barrel or container 313. The two compartment syringe is especially adapted for use with medicament solutions which are not storage stable in the form in which they are to be injected. In the two compartment syringe of the present invention, the stable components of such a medicament solution can be stored separately and can be mixed just prior to use, thereby providing an extended shelf life assembly. In the present instance, the outer barrel houses a granular or liquid substance and the inner barrel contains the liquid diluent. The inner and outer barrels are preferably made of glass but may also be constructed of a suitable transparent plastic material. The outer container 310 is formed at its discharge end with extension means 310a telescopically receiving a cap or cover 310b which normally provides a sealed closure for the discharge end of the outer container but which is capable of being readily removed to permit the hub of a needle to be mounted on the extension 310a when the syringe assembly is to be used. The inner barrel mounts at its discharge end a plunger 314 which is best illustrated in FIG. 13. This plunger, which may be made of a resilient material such as rubber, has a cylindrical axial bore 316 extending therethrough and a rupturable dam wall 318 adjacent one end thereof. The outer periphery of the plunger is provided with a series of grooves 320 defining a plurality of spaced ribs 322. The plunger is adapted to be mounted on the discharge end of the inner container 313 and provide an effective seal therewith in the assembled relation.

In the present instance, this is accomplished by forming the discharge end of the inner container 313 with an enlarged bead 325 which is connected to the generally cylindrical body portion of the barrel by a reduced neck 327.

In assembling the components of the syringe and with particular reference to FIG. 9, it is noted that the liquid barrel is telescoped into the dry barrel a predetermined distance allowing about 20% head space in the front end of the dry barrel as illustrated. To accomplish this, the plunger rod may be initially assembled to the liquid barrel plunger or diaphragm and then disassembled for purposes of packaging and shipment. Now when it is desired to mix the diluent and dry or liquid product, the plunger rod is simply reassembled and pushed forward into the liquid barrel. The hydraulic force thus exerted causes the diaphragm on the dry plunger to expand and eventually rupture allowing the diluent to flow into the dry or liquid barrel. Continued forward movement of the plunger rod expels the diluent until it has been completely evacuated into the dry barrel. The base of the plunger rod is now flush with the base of the liquid barrel. As the diluent is expelled, the result in increase in pressure forces the dry barrel to move forward automatically providing room for both diluent and product within the dry barrel while maintaining the 20% head space needed for effective mixing. The emptied liquid barrel now becomes the plunger rod and after the needle is assembled to the front end of the dry barrel, the syringe can be evacuated of air, inserted, aspirated and injected in the normal manner.

There is illustrated in FIGS. 14,14a,15 a modified form of diaphragm assembly for use in a syringe of the type illustrated in the previously described embodiment. This assembly also includes an outer barrel or container 400 constructed similarly to the container 300 (FIGS. 9-13) and having a removable cap 410b which fits over extension 410a to normally seal the discharge end of the outer container and an inner barrel or container 413 which has a reduced neck as at 415 defining a shoulder 423 and an enlarged bead 417 at the discharge end thereof. In the present instance, the discharge end of the inner container mounts a rubber plunger 414 which prior to assembly has a cylindrical bore 416 (see FIG. 15d) extending therethrough and has a plurality of circumferentially extending axially spaced serrations or ribs 420 in its outer surface which are in sealing engagement with the inner surface of the outer container 400 as illustrated. The bore 416 of the plunger is of a size so that when it is mounted on the enlarged bead 417 at the discharge end of the inner container there is an interference fit and a tight sealing relation established in the manner shown. The fit permits movement of the plunger 414 axially relative to the outer container to afford normal operation of the syringe assembly.

In accordance with this embodiment of the invention, the diaphragm 418 which normally closes the discharge end of the inner container or barrel is cup-shaped and preferably made of an inert material such as Teflon. The outer face 419 of the diaphragm overlies the discharge end of the barrel and the side wall or skirt 419a closely conforms to the periphery of the bead 417 and the diaphragm is firmly seated in place by engagement between the bead and the inner wall of the rubber plunger. Depending on the magnitude of the seating force, as determined by the thickness of the diaphragm, the diameter of the plunger-bore, the fit between the plunger and the inside of the barrel 410, etc., and the manner in which the diaphragm 419 is formed, the diaphragm 419 will either partially slip off, as illustrated in FIG. 15, or the diaphragm 419 will burst, as illustrated in FIG. 15b, when hydraulic pressure is applied rightward to the diaphragm upon displacement of the piston in the rightward direction. If desired, the diaphragm 419 may be provided with a central partial scoring defining a localized weakened area 419c as illustrated in FIG. 15e to facilitate bursting.

For a predetermined dimensional relationship of the plunger bore 416 and the outer diameter of the bead 417 of the inner barrel, the configuration and arrangement of the diaphragm may be such to provide controlled slip off or controlled bursting upon increase of hydraulic pressure in the inner container through actuation of the piston plunger 430a. For example, in a syringe assembly wherein the plunger 414 (FIG. 15d) has a central through bore of about 0.225 inches in diameter and the outer diameter of the bead 417 is between approximately 0.281 inches and 0.300 inches and the Teflon diaphragm is of a thickness of about 0.003 inches, the diaphragm may be of the configuration shown in FIG. 15a to insure slip off. As illustrated, the diaphragm includes an outer disk-like portion 419, overlying the discharge end of the inner container 413, a depending skirt, the skirt having a first portion 435a terminating at the juncture 437a of the bead 417a and shoulder 423a, and a second extended skirt portion 439a which extends beyond the juncture 437a and is firmly seated against the shoulder 423a by the rear portion of the plunger as illustrated. In the embodiment illustrated, half of the skirt comprises the first portion 435a and the other half of the skirt comprises the second extended portion 439a which seats against shoulder 423a. In this manner, when the inner container plunger is actuated, there is a greater seating force on the second portion of the diaphragm than on the first portion, and the diaphragm is displaced in the manner shown in FIG. 15 to permit discharge of the diluent for mixing with the product in the outer container. It is noted that in the various embodiments, the portion of the diaphragm coextensive with the axial extent of the bead 417 may be mechanically bonded thereto in the manner described hereinafter with reference to FIGS. 30-36 inclusive.

There is illustrated in FIG. 15b a modified form of the diaphragm for a two compartment syringe assembly wherein the diaphragm bursts upon actuation of the piston plunger. The overall assembly is identical to that described previously wherein similar parts are designated by similar numbers with a "b" subscript. In the present instance, the diaphragm, as illustrated, is mounted over the discharge end of the inner container and consists of a generally disc-like portion 421b and a generally cylindrical depending skirt snug embracing the outer side wall of the bead 417b and an inwardly directed terminal skirt portion 425b which engages behind the shoulder 427b on the bead 417b in the manner illustrated. In the assembled relation, the plunger 414b presses the terminal flange portion 425b against the rear shoulder 427b on the bead of the barrel to provide a hermetic seal between the contents in the inner and outer containers. Thus in a syringe assembly wherein the plunger bore, bead and Teflon diaphragm are of a dimensional relationship set forth above in connection with FIGS. 15a and 15a', the seating of the terminal skirt portion 425b against the shoulder 423b about its entire periphery produces bursting of the diaphragm upon actuation of the piston plunger for the inner container. The diaphragm may be assembled to the barrel in the manner illustrated in FIGS. 30-36 inclusive and instead of trimming the diaphragm at the juncture of the bead and shoulder as shown in FIGS. 35 and 36, the diaphragm is trimmed at a higher location to define the terminal skirt portion 425b which is adapted to seat againt the rear shoulder of the bead.

The hermetic barrier between the compartments of the inner and outer container provided by the diaphragm and plunger assembly is important to prevent ingress of moisture into the compartment for the dry product in the outer container since moisture could affect the stability of the dry product and render it unsuitable for mixture with the diluent at a later time to provide a solution having the desired therapeutic characteristics. This feature insures an extended shelf life for the assembly.

Now, when it is desired to mix the contents of the inner container and the outer container, the plunger assembly 430a is simply actuated axially inwardly in the inner container and the hydraulic pressure buildup effects displacement of the diaphragm in the manner shown in FIG. 15, or to rupture the same, as shown in FIG. 15a. Displacement and/or bursting of the diaphragm 419 allows the diluent and dry product to be mixed in the outer container 400. A filter assembly 430 may be provided which overlies the outer end of the plunger 414 and which serves to screen any particulate matter which may result from bursting of the diaphragm. The filter assembly as illustrated may comprise an O-ring 432 formed integrally with the filter which snaps into a circumferential groove 434 in the outer axial end face of the plunger 414. This type of filter assembly may be incorporated with the various plunger embodiments illustrated in FIGS. 16-21, inclusive, as well as with the plunger of FIG. 13. All of the diluent is discharged into the outer container by bottoming the plunger assembly 410c. After mixture is completed, the cap 410b is removed, and a needle is mounted on the discharge end of the container 400. The plunger rod assembly 430a is then pushed forward to evacuate all of the air, and now the syringe is ready for injection of the contents into a patient.

The diaphragm of the two-compartment syringe, as illustrated for example in FIG. 14a, may be assembled in a manner to provide total displacement or complete disengagement upon actuation of the piston plunger to discharge the diluent in the manner described above. This can be accomplished by selectively controlling, for example, the force seating the diaphragm at the discharge end of the inner container.

There is illustrated in FIG. 15e, a modified form of piston plunger assembly for the inner barrel of a syringe assembly. The piston plunger 430c comprises a body portion 431c which may be made of a resilient material such as rubber and a facing 432c covering the forward axial end face, made of an inert material, for example, Teflon. By this arrangement, in the syringe assemblies utilizing a diaphragm made of an inert material, as described above, a diluent chamber is provided which is inert chemically with respect to the diluent and the integrity of the diluent in the inner container is maintained thus guaranteeing a longer shelf life of the syringe assembly and obviating any adverse chemical reaction which may take place with certain diluents and a rubber plunger. These chemical reactions could result in producing a therapeutically unsatisfactory solution when mixed with the dry medicament product in the outer container. Of course, the entire piston plunger can be made of an inert plastic material as illustrated in FIG. 1. However, the Teflon faced plunger is more economical, particularly in syringe assemblies that are intended for single use and then discarded. It is noted that the Teflon faced actuating plunger has application in the single compartment as well as the two compartment syringe assemblies illustrated and described herein.

There is illustrated in FIG. 16 a modified form of plunger and barrel terminal end configuration. The plunger designated by the numeral 614 is of generally cylindrical shape having a series of axially spaced circumferentially extending ribs 618 and a diaphragm 620. Adjacent the inner end of the diaphragm is a pocket 622 of frusto-conical shape to accommodate, the bead 619 of the barrel which has a complementary shape.

Figure 17:
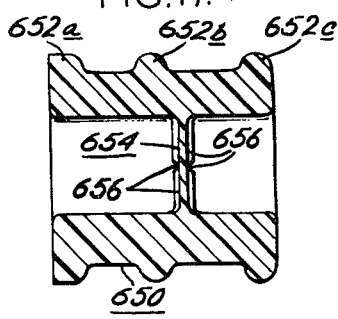
Figure 18:
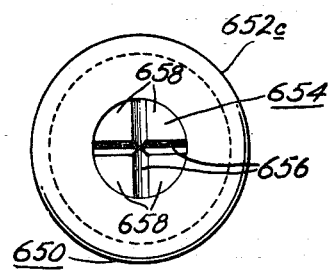

There is illustrated in FIGS. 17 and 18 another form of plunger for use in a syringe in accordance with the present invention. This plunger which is made of an elastic material such as rubber, consists of an elongated generally cylindrical body portion 650 having, in the present instance, three axially spaced ribs 652a, 652b and 652c and a rupturable diaphragm 654 spaced inwardly from opposite axial ends of the body portion. The diaphragm is formed with a localized weakened area to minimize particle formations when the diaphragm bursts and also to provide a more accurate control of force required to rupture the diaphragm. In the embodiment illustrated, the weakened area is provided by a pair of X-shaped V-grooves 656 in opposite faces of the diaphragm leaving four pie-shaped segments 658 of greater cross section. Even though an X-shaped weakened area has been illustrated, it is to be understood that other configurations incorporating the principle of grooves in opposing faces of the diaphragm will also function to provide the control of the bursting pressure as well as minimization of particle formation during bursting of the diaphragm.

Figure 19:
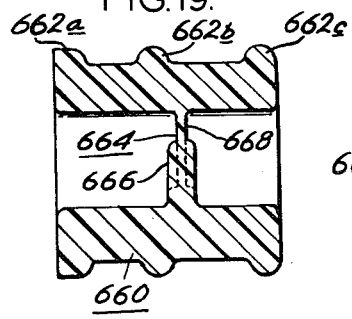
Figure 20:
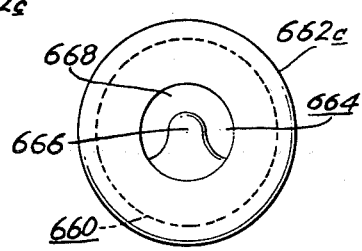

FIGS. 19 and 20 illustrate another form of plunger for a syringe in accordance with the present invention. This embodiment also has the generally cylindrical body portion 660 having the axially spaced circumferential extending ribs 662a, 662b and 662c on its outer periphery and a rupturable diaphragm of circular configuration 664 spaced inwardly from opposite axial ends of the body portion. In the present instance, the diaphragm consists of a teat-shaped section 666 of a greater cross section than the generally C-shaped remainder portion 668.

Figure 21:
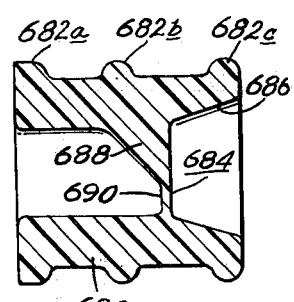

There is illustrated in FIG. 21 a still further embodiment of plunger in accordance with the present invention which comprises a generally cylindrical body portion 680 and the circumferentially extending axially spaced ribs 682a, 682b and 682c and the burstable diaphragms 684. In the present instance the inner walls of the body portion adjacent one end taper outwardly as at 686 and the diaphragm has an enlarged tapered portion 688 which thins out to the burstable membrane 690.

Figure 22:
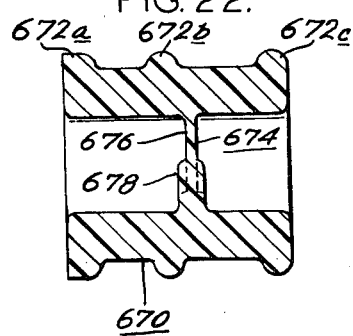
Figure 23:
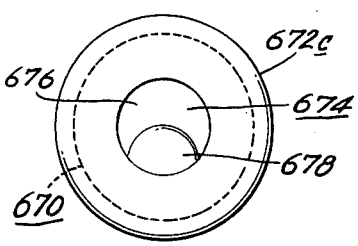

FIG. 22 and 23 illustrate a still further modification of a plunger for a syringe in accordance with the present invention. This embodiment likewise consists of a generally cylindrical body portion 670 having the circumferentially extending axially spaced ribs 672a, 672b and 672c and the circular diaphragm 674 spaced inwardly from opposite axial end of the body portion. In the present instance, the diaphragm consist of a crescent-shaped membrane portion 676 of thinner cross section than the remainder 678 defined by the crescent and the circular trace of the diaphragm.

There is illustrated in FIGS. 24–29 a further embodiment of syringe assembly constructed in accordance with the present invention. The basic syringe assembly is generally designated by the number 700 and is similar in overall construction and arrangement to the previously described embodiment of FIGS. 9–13. inclusive, and includes a primary barrel or syringe container 710 for a dry product and a secondary barrel or syringe container 713 for a diluent which secondary barrel is telescopically engageable in the primary barrel. The primary barrel has a discharge opening at its outer end for a disposable needle assembly 715. A plunger rod 717 having a plunger 719 mounted at its inner end is engageable in the secondary barrel for axial movement therein, the secondary barrel having a discharge opening 721 and mounting a plunger 723 which supports a diaphragm 725 over the discharge end. The diaphragm 725 is preferably made of a resilient, flexible material such as a polytetrafluoroethelene polymer. Teflon is an example of such a material. The diaphragm as illustrated consists of a disc-like portion 725a overlying the secondary opening and the axial end face of the discharge barrel and a skirt 725b of thinner cross section than the disc-like portion 725a. The diaphragm is adapted to be displaced upon pressure build-up in the secondary barrel to permit the diluent to be discharged into the primary barrel and mixed with the dry product. It is noted that in this embodiment, a difference of about 0.004 inches between the outside diameter of the head 730 on the inner barrel, and the inside diameter of the pocket 740 in the plunger 723, provides the desired slip-off action when the syringe assembly 700 is used.

For shipment purposes, the secondary barrel 712 is completely telescoped in the primary barrel 710 with the plunger rod 717 accompanying the unit as a separate element. When it is desired to charge the assembly, the plunger rod 717 is inserted into the plunger 719 and the secondary barrel 713 is retracted. The plunger rod is then advanced forward and the hydraulic force created displaces the diaphragm 725 allowing the diluent and dry product to be mixed in the primary barrel 710. The plunger and rod are bottomed to inject all of the diluent into the primary barrel and mixing of the diluent and dry product is now accomplished in the primary barrel. After mixture is completed, the plunger rod 717 is pushed forward to evacuate all the air in the primary barrel and made ready for injecting.

In accordance with this embodiment of the invention, the plunger 723 for the secondary barrel is provided with an opening 721 having a central axis $A_1$, which, in the present instance, is of circular cross section and which is eccentric to the discharge opening in the secondary barrel.

More specifically the discharge end of the secondary barrel 713 has an enlarged radially outwardly directed bead 730 and a reduced neck portion 732 between the bead 730 and the enlarged body portion of the barrel. The diaphragm 725 is shaped to fit over the bead 730 and thus consists of a circular disc portion 734 overlying the discharge opening 725 and axial end face 736 of the bead 730 and a rearwardly directed circumferential skirt 738 circumscribing the bead 730 and terminating adjacent the lower edge of the bead 730.

The plunger 723 in the present instance, is formed with a pocket 740 with an inlet opening 742 having a central axis $A_2$ which defines a seat for the discharge end of the secondary barrel. The plunger 723 has an elongated bore 744 of circular cross section having a central axis $A_3$ and extending from the pocket 740 to the outer end thereof. The central axis $A_3$ of bore 744 is offset relative to the central axis $A_2$ of the inlet opening 742 and to the central axis $A_1$ of the discharge opening 721 whereby a greater portion of the outer radial wall 747 of the pocket 740 to one side of a plane X—X traverse to a plane Y—Y through the central axis $A_1$ of the discharge opening 721 in the barrel and the central axis $A_3$ of the bore 744 engages a greater portion of the axial end face of the diaphragm than the portion of the wall 747 on the opposite side of the plane X—X. This relationship is shown in FIG. 29 wherein the larger surface area of the wall 747 above the plane X—X which is shaded and generally crescent shaped is designated by the letter L, and the smaller surface area of the wall 747 below the plane X—X is designated by the letter S. By this arrangement during the charging operation when the hydraulic pressure increases due to actuation of the plunger rod 77, the diaphragm 725 tends to remain seated about a first portion of its periphery and releases on a second portion of the circumference diametrically opposed to the first portion illustrated in FIG. 26. In other words, there is a greater seating force holding the diaphragm in the plunger about the portion of the circumference above the plane X—X thereby providing a lever effect pivoting the diaphragm in the manner shown. This insures slip-off or displacement of the diaphragm. Slip-off is desirable because there is no particulation which could contaminate the mixture and which would necessitate use of a filter at the discharge end of the primary barrel.

In the two compartment syringe assemblies described herein, the outer compartment or chamber for the dry medicament product is designated $C_1$ in the drawings, and the inner compartment or chamber for the diluent is designated $C_2$ in the drawings.

Another aspect of the present invention relates broadly to method for applying the diaphragm to the discharge end of a barrel of a syringe assembly. More specifically, the method concerns cold forming of polytetrafluoroethylene polymer film and like materials having similar stretch and adhesion properties to achieve a mechanical bond over the opening in a container or the like made of a variety of materials such as glass, plastic, metal and other materials. A suitable film material is Teflon having a thickness of between 1 and 5 mils. The method steps are best illustrated in FIGS. 30-36 inclusive and for purposes of illustration is shown in conjunction with the application of a thin sheet of Teflon to the discharge end of a barrel of a syringe assembly for example, a single compartment syringe as shown in FIGS. 5 and 6 or the secondary barrel of a two compartment syringe as shown in FIGS. 25 and 26. The barrel as illustrated has a generally cylindrical hollow body portion having a discharge opening 721a at one end, the barrel body portion at the discharge end terminating in a reduced neck 732a and an enlarged outwardly directed bead 730a having an axial end wall 736a. In accordance with the method, the Teflon film $F_t$ is supported between an upper mask 750 and a lower mask 752 each having concentrically aligned openings 754 and 756 therein. With the Teflon film supported in this manner, the member to which the Teflon is to be bonded, in the present instance, the barrel of a syringe, is inserted into the opening of the upper mask 750 with the axial end face 736a confronting the Teflon sheet material and pressed downwardly whereby the unsupported portion of the Teflon film in the area of the aligned openings of the masks is stretched and conforms to the shape of the lower end of the barrel in the manner illustrated. More specifically, it has been found that the disc-like portion of the Teflon overlying the axial end face 736a of the barrel stretches only slightly and that the tent-like area of the unsupported portion of the film designated by the numeral 757 extending from the periphery of the axial end face of the barrel to the edge of the opening in the lower mask stretches considerably up to 200% and conforms to the side wall of the bead 730a. Thereafter, the barrel and, in the present instance, the upper mask is retracted and the Teflon is sheared at the base of the shoulder at the lower discharge end of the barrel by suitable shearing apparatus which comprises a pair of opposed knives 760,760 which are moved toward one another and rotated through 180° relative to the barrel to sever the Teflon. It is noted that in FIG. 35 the knives 760,760 are coplanar so that the skirt portion of the diaphragm is of a predetermined length. However, when it is desired to cut the diaphragm so that it will slip partially off, as illustrated in FIG. 15a and 15a1 the shearing apparatus is modified as illustrated in FIG. 35a by disposing the knife 760a in a higher plane than the plane of its companion knife 760b. The knife 760b is aligned with the juncture 437a, and the knife 760a is aligned with the reduced neck portion 415. Thus, when the knives 760a and 760b are rotated relative to the barrel to sever the Teflon, the diaphragm and barrel assembly illustrated in FIG. 15a and 15a1 are produced. The opening 754 in the upper mask is preferably of a larger diameter than the opening 756 in the lower mask to provide a greater area of unsupported film to preclude fracturing the Teflon sheet material during the forming operation. The barrel is then withdrawn and the film is retained by means of the mechanical bond and once so attached, it will remain until such time as force or pressure is applied even when subjected to a variety of environmental conditions. It is noted the diaphragm provides a hermetic seal. It has been found that Teflon is a particularly suitable material for forming a bonded member in this fashion since it stretches up to 200 or 300% without fracturing and in a stretched condition, does not return to its original shape. In applications such as in the present case it is highly desirable to form a bond in this fashion since it does not employ any bonding agents, such as adhesives, which could contaminate the medicament when the diaphragm is burst or slipped off if exposed thereto. Even though the method is described in connection with the formation of a diaphragm for a barrel of a syringe or the like, it is to be understood that mechanical bonding of Teflon or the like material in this fashion can be effectively used for other purposes.

There is shown in FIGS. 37-43 inclusive, another embodiment of bursting syringe assembly in accordance with the present invention. This syringe assembly is a two-compartment syringe and is generally designated by the numeral 800. The syringe assembly includes an outer barrel or container 810 which is open at its upper end and an inner barrel or container 812. The outer barrel forms a compartment 813 for the powder component of the medicament and the inner barrel defines a compartment for the diluent. The outer barrel 810 is normally sealed prior to use and has means at its discharge end for mounting a needle assembly 815.

Means is provided for isolating the powder and diluent compartments comprising, in the present instance, a plunger 816 which is mounted over the finish 818 on the inner barrel 812 which presses a diaphragm 820 against the discharge end of the inner barrel. The plunger 816 has a series of ribs 822 on its outer periphery which engage the interior wall of the outer barrel to provide a seal. The bore 824 of the plunger may be a straight through bore of circular cross section having a central axis coincidental with the central axis of the inner barrel or offset in the manner shown. The bore 824 has an enlarged pocket portion 825 of a predetermined axial length and diametral size to snugly embrace the discharge end of the inner barrel and firmly seat the diaphragm against the axial end face in the manner illustrated. In the present instance, the diaphragm 820 comprises a rubber O-ring 826 having a Teflon facing 828 directly engaging the axial end face of the discharge end of the inner barrel. The front face of the plunger 816 has a thin wall 830 extending across the central bore which has a small slit 832 therein which prevents accumulation of the powder products which may accumulate in the bore of the plunger during storage. These accumulations which may cake to a solid mass may prevent thorough mixing of the powder and diluent adversely affecting the strength or characteristics of the medicament.

In the operation of the two compartment syringe described, as noted above, the discharge end of the outer barrel is normally sealed and there is a head space 813 in the powder compartment and the diaphragm normally seals the diluent at the discharge end of the inner barrel. The front wall 830 of the plunger as noted prevents caking or accumulation of powder in the central bore of the plunger. Now when it is desired to mix the components, the plunger rod 835 is simply pressed inwardly and the hydraulic pressure build up causes the diaphragm to rupture in the manner shown in FIG. 39. The diluent then flows into the head space to mix with the powder ingredient. As all of the contents of the inner barrel are expelled, the plunger rod moves rearwardly and the products are mixed in the forward compartment. When the operator desires to use the syringe, the seal (not shown) at the forward end of the outer barrel is either removed or punctured in a suitable manner to permit discharge of the medicament through the needle into the patient.

FIGS. 44 and 45 illustrate a slight modification of the plunger assembly illustrated in FIGS. 37–43 inclusive. In accordance with this embodiment, the front face of the plunger wall 839 is lined with a thin coating 840 of an inert material such as Teflon which as illustrated has a short return flange 842. The front wall 839 is provided with a slit 844 and in this instance the Teflon over cover 840 is imperforate and may be molded to the plunger front wall in a suitable manner to provide an adequate bond to effectively seal the powder compartment from the diluent. Now when the plunger rod is activated axially inwardly to effect a pressure build up in the inner barrel, the Teflon cover 840 which serves as a diaphragm bursts at the slit location in the plunger front wall 839 to permit flow of diluent from the inner barrel through the plunger to the powder compartment. This, of course, results in mixing of the medicament in the manner described above.

There is illustrated in FIGS. 46–53 a still further embodiment of two-compartment syringe in accordance with the present invention. Similar to the two compartment syringe described above, this embodiment generally designated by the numeral 900 includes an outer barrel 910, an inner barrel 912 which nests in the inner barrel and a plunger rod 914. The inner barrel has a plunger 950 mounted at its discharge end and in the assembled relation defines the powder compartment 951 at the forward end of the outer barrel which as illustrated has the requisite head space. The forward end of the outer barrel is normally sealed, in this instance, by a two pointed needle assembly, including a resilient seal 930 and a hub member 932 holding the seal in place over the discharge end of the outer barrel. A needle cap 936 normally fits over the needle assembly and may be actuated downwardly when it is desired to penetrate the seal and activate the syringe for discharge of the contents.

In accordance with this embodiment of the invention the plunger 950 mounted on the discharge end of the inner barrel has a central bore 952 and an enlarged pocket 954 at its inner axial end. The plunger also has a series of four ribs on its outer periphery two inner ribs 956 and two enlarged ribs 958 at oppsite axial ends. The diaphragm assembly generally designated by the numeral 960 includes a short sleeve 962 made of a resilient material such as rubber which has a short return flange 964 at its inner end which engages under the enlarged finish 966 of the inner barrel. The sleeve also has a radially inwardly directed flange 970 at its opposite end and a thin diaphragm 972 mounted over the front end of the sleeve in the manner illustrated in FIG. 49.

The sleeve is initially assembled to the inner barrel and then with the sleeve in place it is pressed into the pocket 954 in the plunger. The parts are suitably dimensioned so that when the plunger is inserted into the outer barrel there is a tight seal created preventing leakage of the diluent from the discharge end of the inner barrel.

The syringe is used in essentially the same manner as the one described above. Accordingly, when it is desired to mix the diluent and powder product, the plunger rod 914 is simply actuated downwardly to create hydraulic pressure sufficient to burst the diaphragm 972 and continued movement of the plunger rod inwardly fills the front compartment where the diluent and powder product are mixed. Now when the syringe is ready for use the needle cover is pressed inwardly whereby the inner needle penetrates the seal at the discharge end of the outer barrel and permits discharge of the medicament by the user from the syringe into the patient. Note that in this embodiment, the plunger also has a front wall 974 which extends over the central bore 952 in the plunger and prevents caking or accumulation of the dry powder therein during storage. The wall has a slit 976 to permit flow of the contents in the manner illustrated.

Summarizing the features and operation of the two-compartment syringe in accordance with the present invention and with specific reference to the syringe assembly shown in FIG. 46, it is important to the operation of the syringe in the manner described that there be an air-tight seal at the discharge end of the outer barrel and that the compartment for the powder medicament defined in part by the plunger on the inner barrel have the head space 951. In this manner when the user, for example, a nurse, desires to mix the components of the medicament, the syringe outer barrel is rested in one hand, for example, the left hand, and the plunger rod 914 is urged axially inwardly in the inner barrel whereupon the plunger 914a effects an increase in internal pressure sufficient to effect bursting of the diaphragm 972 to permit discharge of the diluent into the powder compartment. As diluent fills the powder compartment, the air is displaced to the inner compartment and the plunger 950 and inner barrel are moved rearwardly in the outer barrel. When the plunger 914a is bottomed in the inner barrel and the contents are thoroughly mixed, the cap 936 is then pressed downwardly so that the inner end of the needle pierces the seal 930 to establish fluid communication with the mixed medicament. The cap 936 is then removed to expose the outer end of the needle. The nurse then pushes the plunger 950 forwardly to expel any air in the syringe. The syringe is then ready for use to inject into a patient.

The above arrangement and the operation of the syringe are essentially the same with the slip off diaphragm.

What is claimed is:

1. A container for a syringe assembly or the like comprising an elongated generally cylindrical body portion having a discharge opening at one end, a diaphragm mounted over said discharge opening and means engageable with said diaphragm having a bore therein with a central axis offset relative to the central axis of said discharge opening whereby increase in pressure in said container effects displacement of at least a portion of said diaphragm to permit flow through said discharge opening.

2. A container as claimed in claim 1 wherein said means consists of a plunger mounted on the discharge end of said container.

3. A container as claimed in claim 1 made of glass and wherein said diaphragm is a polytetrafluoroethylene polymer mechanically bonded to said container adjacent the discharge end thereof.

4. A container as claimed in claim 3 wherein said discharge end is formed with a radially outwardly extending bead and wherein said diaphragm includes a disc-like portion overlying said discharge opening and a circumferential skirt projecting from said disc-like portion adhering to the overlying said bead.

5. A syringe assembly comprising at least one container with a discharge opening at one end and means actuatable relative to said container for dispensing contents of the container through the discharge opening, a diaphragm positioned over said discharge opening and mounting means for mounting said diaphragm over said opening to normally seal said discharge opening and operable upon pressure build-up in said container to expose said discharge opening to permit dispensing of contents of the container therethrough, said diaphragm being imperforate at least in the area overlying said discharge opening of a predetermined uniform cross-section in the area overlying said discharge opening and said increase in internal pressure being the sole means for exposing said discharge opening.

6. An assembly as claimed in claim 5 wherein the discharge end of said container is provided with a circumferentially extending radially outwardly directed bead and has a reduced neck portion defining a generally radially extending shoulder and wherein said diaphragm includes a face portion overlying the discharge opening and a skirt depending from said face portion, at least a terminal portion of said skirt overlying said shoulder and seated against said shoulder by said mounting means.

7. An assembly as claimed in claim 6 wherein the terminal portion of said skirt overlies said shoulder about its entire periphery.

8. An assembly as claimed in claim 6 wherein half of said terminal portion of said skirt overlies said shoulder and the other half thereof terminates adjacent the juncture of the bead and shoulder.

9. An assembly as claimed in claim 6 wherein said portion of the diaphragm overlying said discharge opening is partially scored.

10. A syringe assembly comprising at least one container with a discharge opening at one end and means actuatable relative to said container for dispensing contents of the container through the discharge opening, a diaphragm confronting said discharge opening, means mounting said diaphragm in a manner to normally seal said discharge opening, said diaphragm being imperforate at least in the area overlying said discharge opening, said mounting means engaging said diaphragm in a predetermined manner whereby upon increase in internal pressure upon actuation of said means for dispensing contents of the container, at least a portion of said diaphragm is released from said mounting means to expose said discharge opening to permit discharge of contents therethrough.

11. A syringe assembly comprising at least one container with a discharge opening at one end and means actuatable relative to said container for dispensing contents of the container through the discharge opening, a diaphragm confronting over said discharge opening, means mounting said diaphragm in a manner to normally seal said discharge opening, said diaphragm being imperforate at least in the area overlying said discharge opening, said mounting means engaging said diaphragm in a predetermined manner whereby upon increase in internal pressure upon actuation of said means for dispensing contents of the container, a portion of said diaphragm is released from said mounting means and a portion remains held by said mounting means thereby to expose said discharge opening to permit discharge of contents therethrough.

12. A syringe as claimed in claim 11 wherein said mounting means comprises a plunger having a bore extending therethrough and engageable with said container to seat said diaphragm against the surface of the container surrounding said discharge opening and wherein the released portion of said diaphragm remains within the bore in said mounting means.

* * * * *